United States Patent [19]

Heckelsberg

[11] 4,317,948
[45] Mar. 2, 1982

[54] PRODUCTION OF BRANCHED HYDROCARBONS
[75] Inventor: Louis F. Heckelsberg, Bartlesville, Okla.
[73] Assignee: Phillips Petroleum Company, Bartlesville, Okla.
[21] Appl. No.: 132,556
[22] Filed: Mar. 21, 1980
[51] Int. Cl.$^3$ .................................................. C07C 2/08
[52] U.S. Cl. ............................ 585/329; 585/255; 585/510; 585/512; 585/525
[58] Field of Search .............. 585/16, 18, 255, 329, 585/510, 525, 12, 512

[56] References Cited

U.S. PATENT DOCUMENTS

| | | | |
|---|---|---|---|
| 3,393,251 | 7/1968 | Fenton | 585/510 |
| 3,485,881 | 12/1969 | Zeuch | 585/513 |
| 3,676,520 | 7/1972 | Heckelsberg | 585/647 |
| 3,865,892 | 2/1975 | Zeuch | 585/523 |
| 3,890,402 | 6/1975 | Stapp | 585/510 |
| 3,997,621 | 12/1976 | Brennan | 585/525 |
| 4,143,087 | 3/1979 | Bamforth et al. | 585/510 |

OTHER PUBLICATIONS

Greassley, Accounts of Chemical Research, vol. 10, pp. 332–339 (1977).

*Primary Examiner*—Curtis R. Davis

[57] ABSTRACT

A mixed olefin feedstock obtained from disproportionating $C_8$ to $C_{18}$ 1-olefins can be used as such for a dimerization process to produce branched hydrocarbons that are useful as lubricating oils or greases.

7 Claims, 1 Drawing Figure

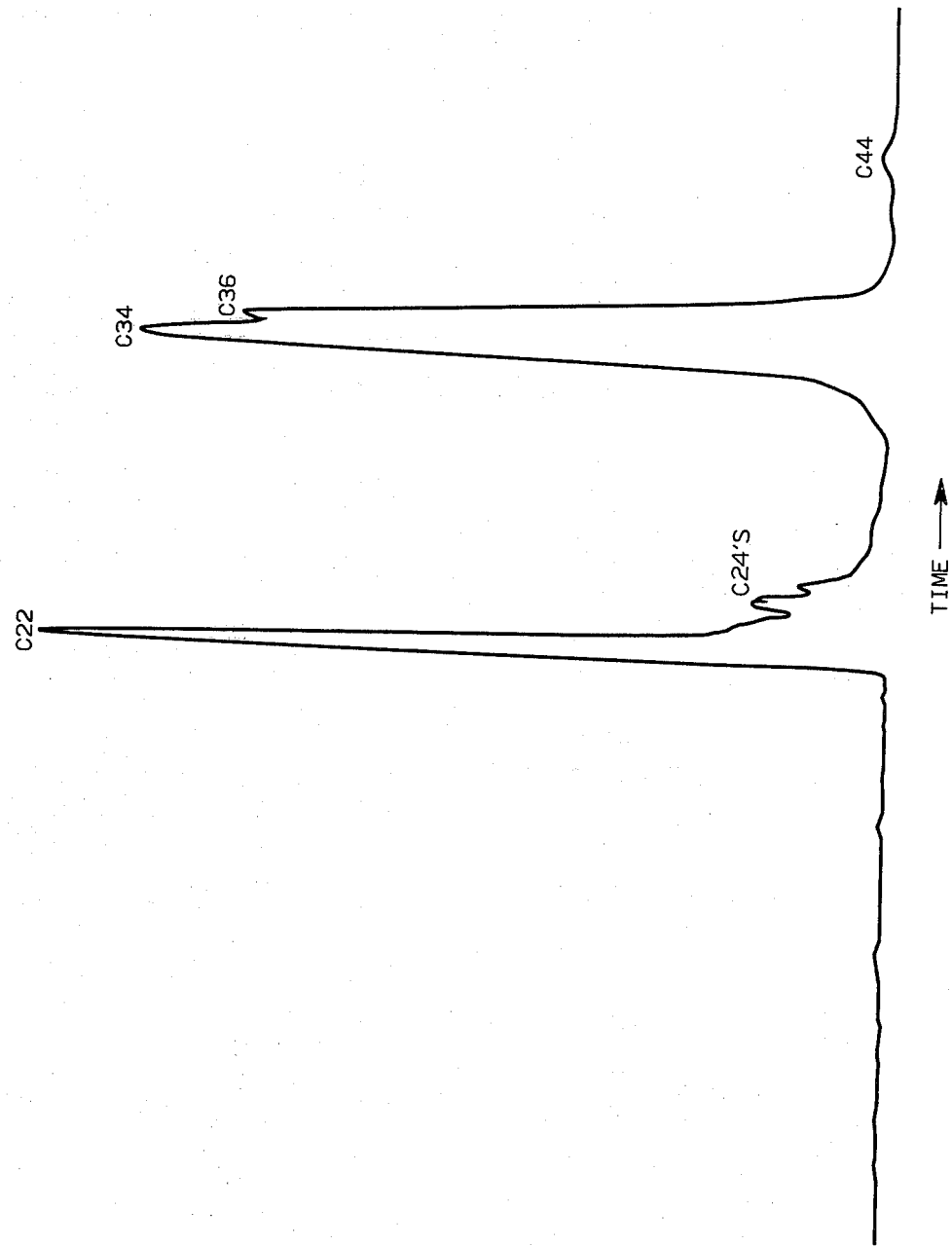

PRODUCTION OF BRANCHED HYDROCARBONS

This invention relates to the production of branched hydrocarbons from olefins. More specifically, the invention relates to the conversion of essentially unbranched monoolefins to branched hydrocarbons. Another aspect of this invention is the production of hydrocarbons useful as lubricating oils and greases.

BACKGROUND OF THE INVENTION

Hydrocarbon conversions and particularly the reactions of olefins constitute a very important section of organic chemistry. The 1-olefins can be polymerized to high polymers, they can be alkylated to high octane fuels and they can be oligomerized to oils.

Lubricating oils have been refined in recent years to match the increasing demands concerning their performance. Not only many additives have been developed for lubricating oils, but also entirely synthetic oils have been produced which exhibit special properties not found in oils produced from crude petroleum alone.

One of the key features in many chemical reactions is the desired purity of the end product. This feature is particularly difficult to achieve in hydrocarbon conversion reactions. The larger the hydrocarbon molecules are, the more difficult it becomes to perform a reaction with only one or two reaction products resulting therefrom. Particularly, producing a hydrocarbon oil with a well defined molecular weight and structure is a continuing goal in the petrochemical industry. Such pure oils can then be used as such or blended into other mixtures with reproducible and desirable properties.

As a general rule, olefins become less reactive the larger their molecular weight and the more the double bond is surrounded by atom groups larger than hydrogen. Thus, generally, 1-olefins are more susceptible to for instance dimerization than internal olefins and lighter olefins oligomerize more readily than heavier olefins.

STATEMENT OF THE INVENTION

It is one object of this invention to provide a process for the production of branched hydrocarbons from essentially straight chain olefins.

Another object of this invention is to convert olefins of vastly different properties to a useful branched hydrocarbon.

It is a further object of this invention to provide a process for producing hydrocarbons useful in the lubricating technology of lubricating oils or greases.

Other objects, advantages, details, features and embodiments of this invention will become apparent to those skilled in the art from the following description of the invention and the appended claims.

In accordance with this invention it has been found that a mixed olefin feedstock when subjected to a dimerization reaction results in useful branched hydrocarbons, both with a relatively high conversion rate and selectivity. The mixed olefin feedstock used in the process of this invention contains as its main olefins a relatively heavy internal monoolefin and a relatively light mono-1-olefin. Roughly, the molecular weight of the mono-1-olefin is ½ of the molecular weight of the internal monoolefin. It was surprisingly found that the lighter 1-olefin and the approximately twice as heavy internal olefin can be brought to codimerize to a substantial extent.

Thus, in accordance with a first embodiment of this invention, there is provided a process for producing branched hydrocarbons having at least 20 carbon atoms per molecule. This process comprises codimerizing a mixed olefin feedstock comprising a first olefin component of one or more 1-olefins having the formula $$R''\text{—CH}=\text{CH}_2 \tag{1}$$

and a second olefin component of one or more internal olefins having the formula $$R\text{—CH}=\text{CH—R}' \tag{2}$$

wherein R, R' and R'' which can be the same or different are alkyl radicals of 6 to 16, preferably 12 to 16 carbon atoms, with a dimerization catalyst under dimerization conditions to form a mixture containing said branched hydrocarbon. Generally, the number of carbon atoms in all the different R+R' together approximately equals the number of carbon atoms in all the different R'' radicals times two. The preferred alkyl radicals are n-alkyl radicals and most preferably R, R', R'' are the same alkyl radicals. The branched hydrocarbon is then separated from this mixture.

The mixed olefin feedstock that is utilized in accordance with this invention for the simplest case of only one species of 1-olefins present and under idealized conditions can also be described as a bimodular feedstock comprising a 1-olefin component having a first molecular weight and an internal olefin component having a second molecular weight. The mixed olefin feedstock comprises internal olefin molecules and 1-olefin molecules from which the internal olefin has been produced. The molecular weight of the internal olefin produced equals twice the molecular weight of the 1-olefins, less the molecular weight of ethylene. Or in yet other terms, the number average molecular weight ($M_{ni}$) of the internal olefin portion of the mixed olefins feedstock equals roughly twice the number average molecular weight ($M_{no}$) of the 1-olefin portion of the mixed olefin feedstock minus the molecular weight of ethylene, $M_{ni}=2M_{no}-28$. In a preferred embodiment of this invention the mixed olefins feedstock composed of a mono-1-olefin component and an internal monoolefin component is obtained by a disproportionation (metathesis) reaction using the mono-1-olefin component defined above as the olefin feedstock.

In the preferred process of this invention 1-dodecene together with 11-docosene is used as a starting material in the dimerization step. Products containing 34 and 36 carbon atoms are obtained. These olefin products are hydrogenated catalytically before being used as lubricants. The separation of the lighter hydrocarbon from the heavier product is achieved by standard methods such as vacuum distillation.

Thus another embodiment of this invention consists in a process for producing a branched hydrocarbon useful in the lubrication technology from a 1-olefin feedstock.

This process comprises contacting a 1-olefin liquid feedstock as defined above in Formula (1) with a disproportionation catalyst under disproportionation conditions to produce a mixed olefin liquid containing both 1-olefin and internal olefin, and contacting this mixed olefin liquid after removal from the disproportionation catalyst with a dimerization catalyst under dimerization conditions to form an oil useful in lubrication. The 1- olefin and the internal olefin are characterized by the formulae given above.

METATHESIS STEP

In the disproportionation or metathesis step of the combined process of this invention alpha olefins can be used that have 8 to 18 carbon atoms, preferably those that have 10 to 16 carbon atoms. Examples for such olefins are 1-octene, 1-nonene, 1-decene, 1-undecene, 1-dodecene, and 1-octadecene, and mixtures thereof. The normal isomers of these olefins are preferred, although small concentrations of branched isomers can be present. Branched alpha olefins reduce the viscosity index of the oil produced and hence are less desirable components of the starting material.

The initial step of the combined process is the metathesis or disproportionation of alpha olefins to produce a larger internal olefin as follows:

$$CH_2=CHR + CH_2=CHR' \rightarrow C_2H_4 + RCH=CHR'$$

where R and R' are alkyl radicals, preferably n-alkyl radicals, having 6 to 16 carbon atoms. In this reaction it is very desirable to prevent or minimize isomerization of the double bond in the olefin product.

If a small degree of isomerization in the metathesis should occur it is contemplated that this will not shift the double bond by more than two carbon atoms. In other words, R' in the internal olefin may have one or two carbon atoms more (less) than R' of the starting 1-olefin, and correspondingly R in such an internal olefin will then have one or two carbon atoms less (more) than R of the starting 1-olefin, without leaving the scope of this invention.

Consequently the metathesis reaction is preferably effected at a mild temperature, and with a catalyst useful under mild disproportionation conditions, such as one comprising an oxide of rhenium. U.S. Pat. No. 3,676,520 discloses such a catalyst. The presently preferred disproportionation catalyst is $Re_2O_7$ on alumina.

The temperature for the metathesis reaction can be from about 0°–50° C.; preferably it will be between 20°–30° C.

The pressure for the metathesis reaction can be from about 0.01 to 2 atmospheres absolute ($1 \times 10^3$ to $2 \times 10^5$ Pa). For convenience atmospheric pressure is preferred. These relatively low pressures permit continuous or frequent removal of the ethylene produced in the reaction. Without its removal the internal olefin can be cleaved to regenerate the alpha olefins via the reverse metathesis reaction.

Olefin metathesis can be effected continuously or batchwise; for this process the batchwise mode is preferred. Using a catalyst as disclosed in the above identified patent, the weight ratio of alpha olefin to catalyst can range from 1:1 to 100:1. The preferred ratio is about 10:1 to 50:1. It is generally impractical to convert all the alpha olefins because of diminishing reaction rates. However, contact time between catalyst and olefin for batchwise reaction can range between about 1–1000 hours; preferably the contact time is 10–500 hours.

If continuous metathesis is to be effected, catalyst and conditions disclosed in U.S. Pat. Nos. 3,658,927 and 3,586,731 can be used. The former teaches catalysts supported on alumina and the latter teaches catalysts supported on silica. These catalysts are treated with alkaline materials that reduce or destroy catalyst acidity that causes double bond isomerization as described in detail in U.S. Pat. No. 3,586,731. Use of the lower temperatures cited in these patents will help to minimize the undesirable isomerization. The metathesis catalyst is frequently used in a fixed bed reactor.

The metathesis step described above produces an olefin mixture comprising internal olefins as well as unreacted 1-olefins. In addition to the approximate average molecular weight relationship between these two olefins given above, the olefin mixture that constitutes the feedstock for the following dimerization step to be described can be also characterized by the composition. The preferred feedstock will contain about 10 to about 50 weight percent 1-olefins and about 90 to about 50 weight percent of internal olefins. The weight percentages are based on the total olefin content as 100 percent.

CODIMERIZATION STEPS

A codimerization reaction between an alpha olefin and the internal olefin $R-CH=CH-R'$ whose preparation was described above is effected to prepare the product of this invention. In this reaction an olefin molecule having three approximately equally sized normal alkyl groups is made. After the hydrogenation, the composition can be used as a lubricating oil.

The codimerization reactions are effected by catalysts that have been disclosed in U.S. Pat. No. 3,485,881. Suitable reaction times and temperatures for codimerization are given there. The composition of the olefin mixture to be codimerized can range from about 0.2 to 10 moles of alpha olefin per mole of internal olefin. To maximize the yield of the product of this invention the olefin mixture will preferably contain at least about one mole of alpha olefin per mole of internal olefin.

Recovery and Purification of the Product

To obtain the desired physical properties in the synthetic lubricant it is frequently desirable to distill the mixture remaining after the dimerization step. The concentration of unreacted internal olefin is generally small but, after removal of the dimerization catalyst, it can be removed by distillation and returned to the dimerization process.

In the preferred embodiment of this invention this distillation step is done by heating the hydrocarbon mixture to a temperature usually in the range of 350° C. to 400° C. The temperature is between the boiling point of the highest boiling internal olefin and the boiling point of the lowest boiling product compound.

Product having unacceptable high molecular weight preferably is removed by vacuum distillation. The hydrocarbon oil in this process is removed as the distillate whereas the undesirably high molecular weight product is removed as the bottom product from a distillation column. The vacuum distillation is usually carried out under a pressure of 0.01 torr to 100 torr, preferably 1–5 torr, and by heating the product to about 315° C. The thus purified and evaporated oil is recondensed and recovered.

Prior to or after the vacuum distillation the oil produced is generally catalytically hydrogenated. This hydrogenation is done in a conventional procedure such as the one described in U.S. Pat. No. 2,270,303. Typical hydrogenation catalysts that can be used are Ni on alumina, cobalt molybdate on alumina, Pd, Pt, or Ru on alumina or carbon, but not acidic supports. The contacting of the oil produced with hydrogen and the hydrogenation catalyst is preferably carried out while the hydrocarbon oil is in the vapor phase as the distillate coming from the vacuum distillation for removing the high molecular weight product described above.

Any U.S. Patent referred to in this specification, for further details consistent with this specification is insofar incorporated into this specification by reference.

EXAMPLE I

The following example illustrates the steps of the process to prepare the lubricant of this invention.

Catalyst for the metathesis step, comprising 13.90 g of 9 percent rhenium heptoxide ($Re_2O_7$) on alumina, was heated in flowing air for 3 hours at 500° C., then cooled to ambient temperature under dry helium. It was transferred to a 2-liter flask that had been oven-dried at 120° C. and flushed with helium; the flask was then closed with a rubber septum, and 600 g of 98% 1-dodecene (Aldrich Chemical Co.) was introduced via a syringe. A small hypodermic needle in the closure permitted ethylene produced in the metathesis reaction to escape. The olefin mixture was allowed to stand at ambient temperature (about 25° C.) and was sampled periodically for GLC analysis. Results of the analyses are shown in Table I.

TABLE I

| Reaction time, hours | 140 | 260 | 340 |
|---|---|---|---|
| Lighter than $C_{12}$, wt. % | trace | trace | trace |
| $C_{12}$ | 53.5 | 37.5 | 36.4 |
| Between $C_{12}$–$C_{22}$ | 1.1 | 1.2 | 1.6 |
| $C_{22}$ | 46.4 | 61.3 | 62.0 |
| Heavier than $C_{22}$ | trace | trace | trace |

GLC analyses of the escaping gas showed it to be ethylene only. Three hundred mL of the olefin mixture having the composition shown in the final column of Table I were codimerized catalytically. The catalyst was prepared by combining, in a dry 2-liter flask, 30 g bis(triphenylphosphine)dichloronickel, 600 mL of cyclohexane, and 180 mL of 25% ethylaluminum dichloride in n-hexane. After standing 30 minutes the olefin mixture was added. The dimerization reaction mixture stood at ambient temperature for 70 hours and then several mL of water was added to deactivate the catalyst. The mixture was then dried over 3A molecular sieve, filtered, and charged to a kettle for vacuum distillation. In addition to obtaining three overhead fractions plus residue in the still pot, a dry ice trap fraction was obtained that was not condensible in the product receiver but kept these vapors from the vacuum pump oil. Results of the distillation together with GLC analyses of the fractions are summarized in Table II. Indicated temperatures have been corrected to normal boiling points.

TABLE II

| | Dry Ice Trap | Fraction #1 | Fraction #2 | Fraction #3 | Residue |
|---|---|---|---|---|---|
| Weight, g | 337.5 | 121.8 | 8.0 | 153.7 | 27.0 |
| Boiling range, °C. | | IBP–212 | 212–377 | 377–532 | 532 |
| GLC analysis, wt. % | | | | | |
| n-Hexane | 17.7 | 15.2 | 0 | 0 | |
| cyclo-hexane | 78.0 | 75.5 | 0 | 0 | |
| $C_{12}$ | 4.0 | 8.6 | 64.2 | 1.0 | |
| $C_{14}$ | 0.3 | 0.7 | 20.0 | 1.0 | |
| $C_{22+24}$ | | | 15.8 | 72.0 | |
| $C_{34}$ | | | | 24 | |
| $C_{40+}$ | | | | 2 | |

Fraction #3 which contained the hydrocarbons that would be suitable for use in lubricating oil was diluted with 198 g of dry n-hexane, then hydrogenated in a one-liter autoclave at about 160° C. and 560 p.s.i.g. hydrogen pressure over 0.5 g of 10% Pd on carbon catalyst. Solvent was stripped from the hydrogenated oil by distillation; the oil was then subjected to distillation at reduced pressure. Some pertinent data are presented in Table III.

TABLE III

| Fraction | 1 | 2 |
|---|---|---|
| Wt. % of charge | 43.5 | 28.8 |
| Corr. boiling range, °C. | 373–394 | 388–500 |
| Appearance | Clear | waxy |
| Viscosity, SUS | | |
| at 100° F. | 48.1 | 73.3 |
| at 210° F. | 33.6 | 38.4 |
| Viscosity Index | 180 | 176 |

Fraction 2 was analyzed by GLC in which a 0.125" o.d. ×6' column containing Dexsil 300 supported on Chromosorb was used. The chromatogram obtained is shown in the FIGURE. The concentration of the principal components found in this analysis is

TABLE IV

| $C_{22}$ | 22.0 wt. % |
|---|---|
| $C_{23}$–$C_{33}$ | 12.7 wt. % |
| $C_{34}$ | 40.5 wt. % |
| $C_{36}$ | 22.4 wt. % |
| $C_{44}$ | 1.4 wt. % |

The $C_{23}$–$C_{33}$ region appears to consist primarily of isomers of tetracosene made by the dimerization of 1-dodecene. The $C_{34}$ was made by addition of 1-dodecene to 11-docosene. The $C_{36}$ was made by trimerization of 1-dodecene, and the $C_{44}$ was made by dimerization of 11-docosene.

EXAMPLE II

Metathesis of 304 grams of 1-dodecene was performed as described in Example I, using the same quantity of 9% $Re_2O_7/Al_2O_3$ catalyst. After 195 hours the composition of the olefin mixture was

TABLE V

| $C_{<12}$ | 0.7 wt. % |
|---|---|
| $C_{12}$ | 29.6 wt. % |
| $C_{13-21}$ | 7.2 wt. % |
| $C_{22}$ | 62.5 wt. % |

Portions having this composition were contacted with several different nickel-containing catalysts to effect dimerization. The recipes for these tests are summarized in Table VI.

TABLE VI

| Ni Compound* | I $Cl_2(PPh_3)_2Ni$ | II $(PPh_3)_2(CO)_2Ni$ | III $Ni(C_5H_7O_2)_2 \cdot H_2O$ |
|---|---|---|---|
| Wt. Ni compound, g | 0.5 | 0.25 | 0.25 |
| Cyclohexane, mL | 10 | 10 | 10 |
| EADC, mL** | 3 | 3 | 3 |
| Olefin mix, mL | 5 | 5 | 5 |

*Ph is the phenyl radical
**25% ethylaluminum dichloride in n-hexane

In each case the olefin mixture was added to the catalyst 30 minutes after it had been prepared. After standing at about 25° C. for 66 hours the catalyst was destroyed by addition of water and the hydrocarbon phase was analyzed by GLC. The instrument used did not provide as good resolution as the one on which the FIGURE was obtained. Results from its use on these samples are summarized in Table VII.

TABLE VII

|  | I | II | III |
|---|---|---|---|
| $C_{12}$, wt. % | 18 | 20 | 16 |
| $C_{22}$ | 52 | 54 | 50 |
| $C_{30}$–$C_{40}$ | 28 | 25 | 26 |
| >$C_{40}$ | 2 | 1 | 8 |

Reasonable variations and modifications which will become apparent to those skilled in the art can be made in this invention without departing from the spirit and scope thereof.

I claim:

1. A process for producing branched hydrocarbons having at least 22 carbon atoms per molecule comprising
(a) contacting a mixed olefin feedstock comprising a first and a second olefin component both constituting a substantial portion of the total olefin feedstock said first olefin component of one or more 1-olefins having the formula $$R''-CH=CH_2 \qquad (1)$$

and said second olefin component of one or more internal olefins having the formula $$R-CH=CH-R' \qquad (2)$$

wherein R, R' and R" which can be the same or different are alkyl radicals of 6 to 16 carbon atoms, with a nickel containing dimerization catalyst under dimerization conditions to form a mixture containing said branched hydrocarbon comprising olefins codimerized of said 1-olefin with said internal olefin, and
(b) separating said branched hydrocarbon from said mixture.

2. A process in accordance with claim 1 wherein said mixed olefin feedstock comprises the olefin mixture obtained by disproportionating a 1-olefin feedstock having the formula (1) substantially without isomerization.

3. A process in accordance with claim 2 comprising
(a) contacting a 1-olefin having the formula (1) with a disproportionation catalyst under disproportionation conditions to form ethylene and said mixed olefin feedstock,
(b) separating said mixed olefin feedstock from said disproportionation catalyst, and
(c) contacting said mixed olefin feedstock with said dimerization catalyst.

4. A process in accordance with claim 3 comprising continuously removing ethylene from a disproportionation zone wherein said disproportionation step is carried out.

5. A process in accordance with claim 1 comprising
(a) removing said dimerization catalyst from said mixture to produce a hydrocarbon fluid,
(b) subjecting said hydrocarbon fluid to a distillation to remove unreacted 1-olefin and internal olefin from said hydrocarbon fluid leaving a hydrocarbon oil
(c) subjecting said hydrocarbon oil to a vacuum distillation at a temperature above the boiling point of the dimer of said internal olefin under the given pressure of the vacuum distillation to produce an oil vapor and a liquid of high molecular weight components,
(d) condensing said oil vapor to produce a purified hydrocarbon oil.

6. A process in accordance with claim 5 wherein said hydrocarbon oil prior to or after said vacuum distillation step c is contacted under hydrogenation conditions with molecular hydrogen and a hydrogenation catalyst such as to remove essentially all of the olefinic unsaturation from the oil molecules.

7. A process in accordance with claim 3 wherein said 1-olefin used in step a is dodecene-1, wherein said disproportionation catalyst is a rhenium catalyst, wherein said mixed olefin feedstock is a feedstock comprising 1-dodecene and 11-docosene, and wherein said mixture produced comprises $C_{34-36}$ olefins.

* * * * *